United States Patent
Kornblit et al.

(10) Patent No.: US 9,433,907 B2
(45) Date of Patent: Sep. 6, 2016

(54) APPARATUS FOR CONTROLLING THE MOVEMENT OF A LIQUID ON A NANOSTRUCTURED OR MICROSTRUCTURE SURFACE

(75) Inventors: Avinoam Kornblit, Highland Park, NJ (US); Thomas Nikita Krupenkin, Middleton, WI (US); Mary Louise Mandich, Martinsville, NJ (US); Tobias Manuel Schneider, Marburg (DE); Joseph Ashley Taylor, Madison, WI (US); Shu Yang, Blue Bell, PA (US)

(73) Assignee: Alcatel Lucent, Boulogne-Billancourt (FR)

(*) Notice: Subject to any disclaimer, the term of this patent is extended or adjusted under 35 U.S.C. 154(b) by 1011 days.

(21) Appl. No.: 12/370,219

(22) Filed: Feb. 12, 2009

(65) Prior Publication Data

US 2009/0274580 A1 Nov. 5, 2009

Related U.S. Application Data

(63) Continuation of application No. 10/403,159, filed on Mar. 31, 2003, now abandoned.

(51) Int. Cl.
*B01L 99/00* (2010.01)
*B01F 5/06* (2006.01)
(Continued)

(52) U.S. Cl.
CPC ......... *B01F 5/0619* (2013.01); *B01F 13/0076* (2013.01); *B01J 19/0093* (2013.01); *B01L 3/5088* (2013.01); *B01L 3/50273* (2013.01); *B01L 3/502746* (2013.01); *B81B 1/00* (2013.01); *B82Y 30/00* (2013.01); *G01N 21/4788* (2013.01); *G01N 21/552* (2013.01); *B01F 2005/0621* (2013.01);
(Continued)

(58) Field of Classification Search
None
See application file for complete search history.

(56) References Cited

U.S. PATENT DOCUMENTS 4,750,693 A * 6/1988 Lobert et al. ................. 244/200
5,674,592 A 10/1997 Clark et al.
(Continued)

FOREIGN PATENT DOCUMENTS

| EP | 1120164 A2 | 8/2001 |
|---|---|---|
| WO | 9954730 A1 | 10/1999 |
| WO | 03103835 A1 | 12/2003 |

OTHER PUBLICATIONS

Washizu, Masao; "Electrostatic Actuation of Liquid Droplets for Microreactor Applications"; IEEE Transactions on Industry Applications, vol. 34, No. 4, Jul./Aug. 1998.; pp. 732-737.
(Continued)

*Primary Examiner* — Paul Hyun
(74) *Attorney, Agent, or Firm* — Parker Justiss, PC

(57) ABSTRACT

A method and apparatus is disclosed wherein the movement of a droplet disposed on a nanostructured or microstructured surface is determined by at least one characteristic of the nanostructure feature pattern or at least one characteristic of the droplet. In one embodiment, the movement of the droplet is laterally determined by at least one characteristic of the nanostructure feature pattern such that the droplet moves in a desired direction along a nanostructured feature pattern. In another embodiment, the movement of the droplet is determined by either at least one characteristic of the nanostructure feature pattern or at least one characteristic of the droplet in a way such that the droplet penetrates the feature pattern at a desired area and becomes substantially immobile.

10 Claims, 14 Drawing Sheets

(51) Int. Cl.
*B01F 13/00* (2006.01)
*B01J 19/00* (2006.01)
*B01L 3/00* (2006.01)
*B81B 1/00* (2006.01)
*B82Y 30/00* (2011.01)
*G01N 21/47* (2006.01)
*G01N 21/552* (2014.01)
*B41J 2/14* (2006.01)

(52) U.S. Cl.
CPC .............. *B01F 2005/0636* (2013.01); *B01J 2219/00783* (2013.01); *B01J 2219/00833* (2013.01); *B01J 2219/00853* (2013.01); *B01L 2300/089* (2013.01); *B01L 2300/0896* (2013.01); *B01L 2300/166* (2013.01); *B01L 2300/168* (2013.01); *B01L 2400/0406* (2013.01); *B01L 2400/0415* (2013.01); *B01L 2400/0688* (2013.01); *B01L 2400/082* (2013.01); *B01L 2400/088* (2013.01); *B41J 2002/14395* (2013.01); *B81B 2203/0361* (2013.01)

(56) References Cited

U.S. PATENT DOCUMENTS

| | | | |
|---|---|---|---|
| 6,185,961 B1 | 2/2001 | Tonucci et al. |
| 6,338,820 B1 | 1/2002 | Hubbard et al. |
| 6,350,397 B1 | 2/2002 | Heikkila et al. |
| 6,685,841 B2 | 2/2004 | Lopez et al. |
| 6,747,285 B2 | 6/2004 | Schueller et al. |
| 7,005,593 B2 | 2/2006 | Gasparyan et al. |
| 7,048,889 B2 | 5/2006 | Arney et al. |
| 7,156,032 B2 | 1/2007 | Kornblit et al. |
| 7,227,235 B2 | 6/2007 | Kroupenkine et al. |
| 7,618,746 B2 | 11/2009 | Kroupenkine et al. |
| 7,644,402 B1 | 1/2010 | Daynes et al. |
| 7,749,646 B2 | 7/2010 | Hodes et al. |
| 8,124,423 B2 | 2/2012 | Hodes et al. |
| 2002/0125192 A1 | 9/2002 | Lopez et al. |
| 2003/0020915 A1 | 1/2003 | Schueller et al. |
| 2003/0052006 A1 | 3/2003 | Noca et al. |
| 2004/0173506 A1 | 9/2004 | Doktycz et al. |
| 2004/0191127 A1 | 9/2004 | Kornblit et al. |
| 2005/0069458 A1 | 3/2005 | Hodes et al. |
| 2005/0203613 A1 | 9/2005 | Arney et al. |
| 2005/0208370 A1 | 9/2005 | Hodes et al. |
| 2005/0211505 A1 | 9/2005 | Kroupenkine et al. |

OTHER PUBLICATIONS

European Search Report for EP Application No. 04015738 Dated Sep. 15, 2004; 4 Pages.
European Search Report for EP Application No. 04015737 Dated Sep. 15, 2004; 4 Pages.
European Search Report for EP Application No. 04015736 Dated Sep. 15, 2004; 4 Pages.
European Search Report for EP Application No. 04015735 Dated Sep. 15, 2004; 4 Pages.
Kim, Joonwon, et al.; "Nanostructured Surfaces for Dramatic Reductions of Flow Resistance in Droplet-Based Microfluidics"; IEEE, 2002, pp. 479-482.
U.S. Appl. No. 10/803,565, entitled "Reserve Cell Array Nanostructured Battery", filed Mar. 18, 2004.
U.S. Appl. No. 10/803,576, entitled "Nanostructured Battery Having End of Life Cells", filed Mar. 18, 2004.

\* cited by examiner

FIG. 4A
(PRIOR ART)
FIG. 4B
(PRIOR ART)
FIG. 4C
(PRIOR ART)
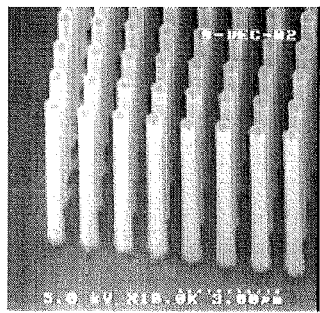 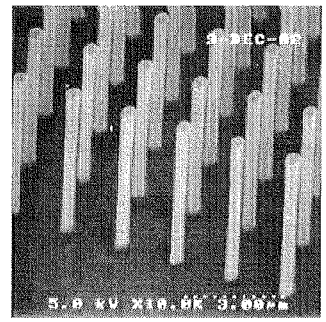 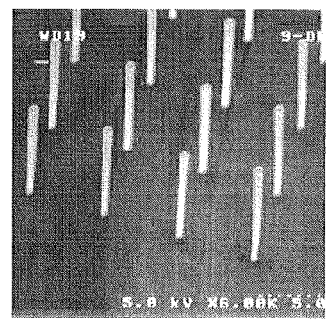
FIG. 4D
(PRIOR ART)
FIG. 4E
(PRIOR ART)
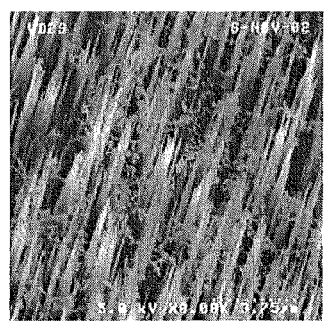 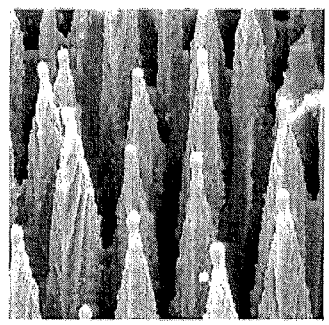

US 9,433,907 B2

APPARATUS FOR CONTROLLING THE MOVEMENT OF A LIQUID ON A NANOSTRUCTURED OR MICROSTRUCTURE SURFACE

This Application is a Continuation of prior application Ser. No. 10/403,159 filed on Mar. 31, 2003 now abandoned, to Avinoam Kornblit, et al. entitled, "METHOD AND APPARATUS FOR CONTROLLING THE MOVEMENT OF A LIQUID ON A NANOSTRUCTURED OR MICROSTRUCTURED SURFACE" currently pending. The above-listed Application is commonly assigned with the present invention and is incorporated herein by reference as if reproduced herein in its entirety under Rule 1.53(b).

FIELD OF THE INVENTION

The present invention relates generally to the motion of liquids disposed on a surface with extremely small, predetermined surface features and, more particularly, to controlling the movement of a liquid on a surface with predetermined nanostructure or microstructure features

BACKGROUND OF THE INVENTION

Many beneficial devices or structures in myriad applications are characterized at least in part by having a liquid that is in contact with at least one solid surface. For example, liquid droplets disposed on surfaces or within channels are the hallmarks of many microfluidic devices, biological/chemical sensors, chemical reactors, optical components, heat dissipation devices, and patterning applications. Many of these devices and applications are characterized in that liquid moves or is caused to be moved while in contact with a surface. Since the characteristics of both the liquid and the surface determine the interaction between the liquid and surface, it is often desirable to understand and control those characteristics to achieve control of the interaction of the liquid with those surfaces This is especially so when the application in question involves relatively small quantities of liquid.

FIG. 1 shows one illustrative prior art embodiment of small liquid droplet 102 disposed on a surface in a way such that it forms a liquid microlens 101. Such a liquid microlens is the subject of copending U.S. patent applications Ser. No. 09/884,605, filed Jun. 19, 2001, entitled "Tunable Liquid Microlens" and Ser. No. 09/951,637, filed Sep. 13, 2001, entitled "Tunable Liquid Microlens With Lubrication Assisted Electrowetting." Both of these copending Patent Applications are hereby incorporated by reference herein in their entirety. The microlens embodiment of FIG. 1 is useful to demonstrate the interaction between any droplet of liquid and the surface on which it is disposed, whether or not the droplet and surface are part of a microlens or another application. In FIG. 1, droplet 102 is a droplet of a transparent liquid, such as water, typically (but not necessarily) with a diameter from several micrometers to several millimeters. The droplet is disposed on a transparent substrate 103 which is typically hydrophobic or includes a hydrophobic coating. The contact angle $\theta$ between the droplet and the substrate is determined by interfacial surface tensions (also known as interfacial energy) "$\gamma$", generally measured in milli-Newtons per meter (mN/m). As used herein, $\gamma_{S-V}$ is the interfacial tension between the substrate 103 and the air, gas or other liquid that surrounds the substrate, $\gamma_{L-V}$ is the interfacial tension between the droplet 102 and the air, gas or other liquid that surrounds the droplet, and $\gamma_{S-L}$ is the interfacial tension between the substrate 103 and the droplet 102. The contact angle $\theta$ may be determined from equation (1):

$$\cos \theta = (\gamma_{S-V} - \gamma_{S-L})/\gamma_{L-V} \qquad \text{Equation (1)}$$

Equation (1) applies to any instance where a droplet of liquid is disposed on a surface, whether or not the droplet is used as a microlens.

In the microlens embodiment of FIG. 1 and in other instances where a liquid is disposed on a surface, it is often desirable to be able to change the shape of the droplet. FIG. 2 shows a prior art microlens 201, similar to the microlens of FIG. 1, whereby the phenomenon of electrowetting is used to change the shape of the droplet by reversibly changing the contact angle $\theta$ between droplet 202 of a conducting liquid and a dielectric insulating layer 203 having a thickness "d" and a dielectric constant $\in_r$. An electrode, such as metal electrode 204, is positioned below the dielectric layer 203 and is insulated from the droplet 202 by that layer. The droplet 202 may be, for example, a water droplet, and the dielectric insulating layer 203 may be, for example, a Teflon/Parylene surface.

When no voltage difference is present between the droplet 202 and the electrode 204, the droplet 202 maintains its shape defined by the volume of the droplet and contact angle $\theta_1$, where $\theta_1$ is determined by the interfacial tensions $\gamma$ as explained above. When a voltage V is applied to the electrode 204, the voltage difference between the electrode 204 and the droplet 202 causes the droplet to spread. The dashed line 205 illustrates that the droplet 202 spreads equally across the layer 203 from its central position relative to the electrode 204. Specifically, the contact angle $\theta$ decreases from $\theta_1$ to $\theta_2$ when the voltage is applied between the electrode 204 and the droplet 202. By using separate electrodes under different parts of the droplet, and varying the voltage to those individual electrodes, spreading of the droplet can be achieved such that the droplet moves from its centered position to another desired position. Such a movement is described in the aforementioned copending '605 and '637 patent applications. The voltage V necessary to achieve this spreading, whether to change the shape of the droplet or its position, may range from several volts to several hundred volts. The amount of spreading, i.e., as determined by the difference between $\theta_1$ and $\theta_2$, is a function of the applied voltage V. The contact angle $\theta_2$ can be determined from equation (4):

$$\cos \theta(V) = \cos \theta(V=0) + V^2(\in_0 \in_r)/(2d\gamma_{L-V}) \qquad \text{Equation (4)}$$

where cos $\theta$ (V=0) is the contact angle between the insulating layer 203 and the droplet 202 when no voltage is applied between the droplet 202 and electrode 204; $\gamma_{L-V}$ is the droplet interfacial tension described above; $\in_r$ is the dielectric constant of the insulating layer 203; and $\in_0$ is $8.85 \times 10^{-12}$ F/M—the permittivity of a vacuum.

In implementations such as the liquid microlens described above, while the surface upon which the droplet is disposed is hydrophobic, the characteristics of that surface are such that the droplet flattens significantly at the area where it comes into contact with the surface. Thus, due to the resulting large contact area between the surface and the droplet, a significant amount of flow resistance is present between the surface and the droplet. This is desirable in the above microlens because, if there were too little flow resistance present, the droplet would freely move and it would become impossible to maintain the droplet in its desired stationary position or shape in the absence of other means for controlling the droplet. However, in many instances, it is often desirable to reduce the flow resistance experienced by a liquid on a surface.

Therefore, recent applications relying on liquids disposed on such surfaces have centered on attempts to reduce the aforementioned flow resistance exerted on the liquid. Many devices, such as those referred to above, can benefit from such a reduced flow resistance because of the resulting significant reduction in the operational power consumption of the devices. One such application is described in "Nanostructured Surfaces for Dramatic Reduction of Flow Resistance in Droplet-based Microfluidics", J. Kim and C. J. Kim, IEEE Conf. MEMS, Las Vegas, Nev., January 2002, pp. 479-482, which is hereby incorporated by reference herein in its entirety. That reference generally describes how, by using surfaces with predetermined nanostructure features, the flow resistance to the liquid in contact with the surface can be greatly reduced.

The Kim reference teaches that, by finely patterning the surface in contact with the liquid, and using the aforementioned principle of liquid surface tension, it is possible to greatly reduce the area of contact between the surface and the liquid. It follows that the flow resistance to the liquid on the surface is correspondingly reduced.

FIGS. 3A-3F show how different, extremely fine-featured microstructure and nanostructure surface patterns result in different contact angles between the resulting surface and a droplet of liquid. FIGS. 3A and 3B show a microline surface and a micropost surface, respectively. Each of the lines 301 in FIG. 3A is approximately 3-5 micrometers in width and each of the microposts 302 in FIG. 3B is approximately 3-5 micrometers in diameter at its widest point. Comparing the microline pattern to the micropost pattern, for a given size droplet disposed on each of the surfaces, the contact area of the droplet with the microline pattern will be greater than the contact area of the droplet with the micropost pattern. FIGS. 3D and 3E show the contact angle of a droplet relative to the microline surface of FIG. 3A and the micropost surface of FIG. 3B, respectively. The contact angle 303 of the droplet 305 on the microline pattern is smaller (~145 degrees) than the contact angle 304 of the droplet 306 with the micropost pattern (~160 degrees). As described above, it directly follows that the flow resistance exerted on the droplet by the microline pattern will be higher than that exerted by the micropost pattern.

FIG. 3C shows an even finer pattern than that of the microline and micropost pattern. Specifically, FIG. 3C shows a nanopost pattern with each nanopost 309 having a diameter of less than 1 micrometer. While FIG. 3C shows nanoposts 309 formed in a somewhat conical shape, other shapes and sizes are also achievable. In fact, cylindrical nanopost arrays have been produced with each nanopost having a diameter of less than 10 nm. Specifically, FIGS. 4A-4E show different illustrative arrangements of nanoposts produced using various methods and further show that such various diameter nanoposts can be fashioned with different degrees of regularity. Moreover, these figures show that it is possible to produce nanoposts having various diameters separated by various distances. An illustrative method of producing nanoposts, found in U.S. Pat. No. 6,185,961, titled "Nanopost arrays and process for making same," issued Feb. 13, 2001 to Tonucci, et al, is hereby incorporated by reference herein in its entirety. Nanoposts have been manufactured by various methods, such as by using a template to form the posts, by various means of lithography, and by various methods of etching.

Referring to FIG. 3F, a droplet 307 disposed on the nanopost surface of FIG. 3C, is nearly spherical with a contact angle 308 between the surface and the droplet equal to between 175 degrees and 180 degrees. The droplet 307 disposed on this surface experiences nearly zero flow resistance. As a result, as is noted by the Kim reference, prior attempts at placing a droplet on such a surface were problematic, as this extremely low flow resistance made it almost impossible to keep the water droplets stationary on the nanostructured surface. As shown in FIG. 5, the reason for this low flow resistance is that the surface tension of droplet 501 of an appropriate liquid (depending upon the surface structure) will enable the droplet 501 to be suspended on the tops of the nanoposts with no contact between the droplet and the underlying solid surface. This results in an extremely low area of contact between the droplet and the surface (i.e., the droplet only is in contact with the top of each post 502) and, hence low flow resistance.

Thus, as exemplarily taught by the Kim reference, prior attempts to reduce flow resistance of liquids through the use of nanostructures have been limited to disposing the droplets in a narrow channel, tube or other enclosure to control the freedom movement of the droplet to within a prescribed area.

SUMMARY OF THE INVENTION

While prior attempts to advantageously dispose a liquid droplet on a nanostructure or microstructure feature pattern have been limited to disposing that droplet in a confining channel, we have realized that it would be extremely advantageous to be able to variably control the movement of a droplet disposed on a nanostructured or microstructured surface without having to place the liquid droplet in a channel. We have also realized that it would be especially advantageous to be able to control the properties of the interface of a liquid droplet with a nanostructured or microstructured surface, such as the amount of flow resistance exerted on the liquid as a result of the contact area between a nanostructured or microstructured surface. Additionally we have realized that in many applications it would be highly advantageous to be able to control the degree of penetration of the droplet inside the nanostructured or microstructured surface.

We have invented a method and apparatus wherein the movement of a liquid droplet disposed on a nanostructured or microstructured surface is determined by at least one intra-pattern characteristic, defined herein below, of the nanostructure or microstructure feature pattern on that surface or at least one characteristic of the droplet. In one embodiment, the lateral movement of the droplet is determined by at least one characteristic of the nanostructure or microstructure feature pattern such that the droplet moves in a desired direction along the feature pattern. To achieve this movement, illustratively, the size, shape, density, or electrical properties of the nanostructure or microstructure are designed such that the contact angle of the leading edge of a droplet is made to be lower than the contact angle of the trailing edge of the droplet to achieve a desired movement.

In another embodiment, the movement of the droplet is determined by either at least one intra-pattern characteristic of the feature pattern or at least one characteristic of the droplet such that the droplet penetrates the feature pattern at a desired area and becomes immobile. This characteristic can be, for example, the surface tension of the droplet, the temperature of either the droplet or the pattern or the voltage differential between the droplet and the feature pattern.

One or both of these embodiments of the present invention are useful in a variety of applications, such as, illustratively, a biological or micro-chemical detector, a chemical reactor, a patterning application, a tunable diffraction grating, a total internal reflection mirror, a microfluidic mixer, a microfluidic pump and a heat dissipation device.

BRIEF DESCRIPTION OF THE DRAWING

FIGS. 4A, 4B, 4C, 4D and 4E show various prior art nanostructure feature patterns of predefined nanostructures that are suitable for use in the present invention;

DETAILED DESCRIPTION

Figure 6:
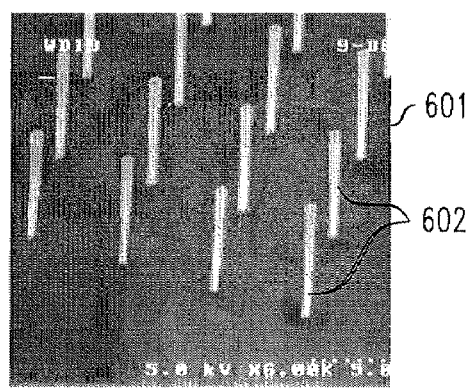
FIG. 6 shows a more detailed view of the prior art nanostructure feature pattern of FIG. 4C.

FIG. 6 shows an illustrative known surface 601 with a nanostructure feature pattern of nanoposts 602 disposed on the surface. Throughout the description herein, one skilled in the art will recognize that the same principles applied to the use of nanoposts or nanostructures can be equally applied to microposts or other larger features in a feature pattern. The surface 601 and the nanoposts 602 of FIG. 6 are, illustratively, made from silicon. The nanoposts 602 of FIG. 6 are illustratively approximately 350 nm in diameter, approximately 6 µm high and are spaced approximately 4 µm apart, center to center. It will be obvious to one skilled in the art that such arrays may be produced with regular spacing or, alternatively, with irregular spacing.

Figure 7A:
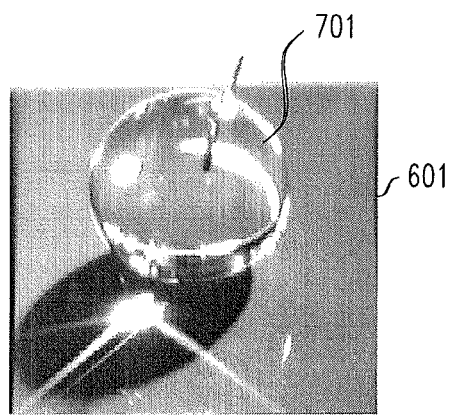
FIGS. 7A, 7B, 7C and 7D show droplets of different liquid having different surface tensions disposed on the nanostructure feature pattern of FIG. 6.
Figure 7B:
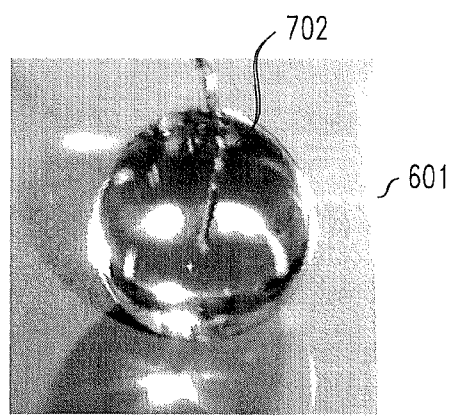
Figure 7C:
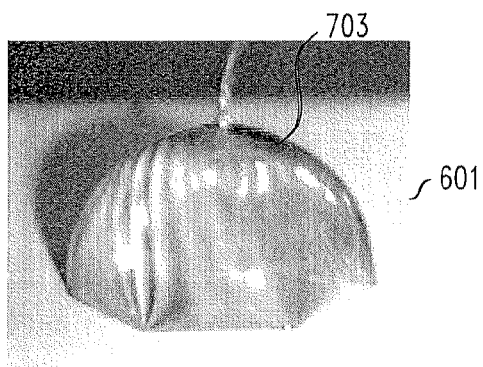
Figure 7D:
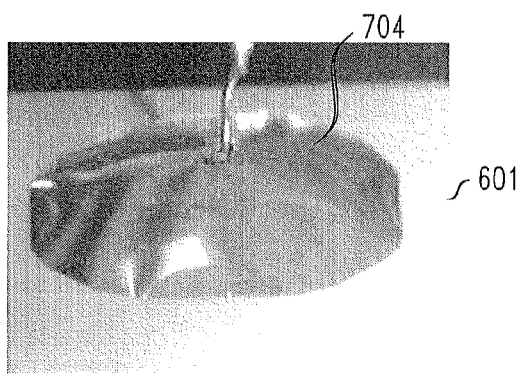

FIGS. 7A, 7B, 7C and 7D show how different liquids behave when disposed on the illustrative surface 601 of FIG. 6. FIG. 7A shows that, when a water droplet 701 with a surface tension ($\gamma$) of 72 mN/m is disposed on the surface 601, the droplet 701 retains a nearly spherical shape for the aforementioned reasons. FIGS. 7B, 7C and 7D show how for liquid droplets 702, 703 and 704, respectively, with decreasing surface tension (ethyleneglycol [$\gamma$=47 mN/m], cyclopentanol [$\gamma$=33 mN/m] and octanol [$\gamma$=27 mN/m], respectively) the droplets spread in increasing amounts over a greater area, with the droplet having the lowest surface tension (droplet 704) spreading to the greatest extent.

As used herein, unless otherwise specified, a "nanostructure" is a predefined structure having at least one dimension of less than one micrometer and a "microstructure" is a predefined structure having at least one dimension of less than one millimeter. The term "feature pattern" refers to either a pattern of microstructures or a pattern of nanostructures. Further, the terms "liquid," "droplet," and "liquid droplet" are used herein interchangeably. Each of those terms refers to a liquid or a portion of liquid, whether in droplet form or not. Additionally, medium, as used herein, is a gas or liquid in which a biological or chemical element may be present, as discussed herein below. Finally, intra-pattern characteristics, as used herein, are defined as a) characteristics of the individual feature pattern elements relative to other elements (as opposed to inter-pattern characteristics, which are macro characteristics of the feature pattern, such as orientation of the entire pattern), or b) certain characteristics of individual feature pattern elements such as shape, size, height and electrical characteristics.

Figure 8A:
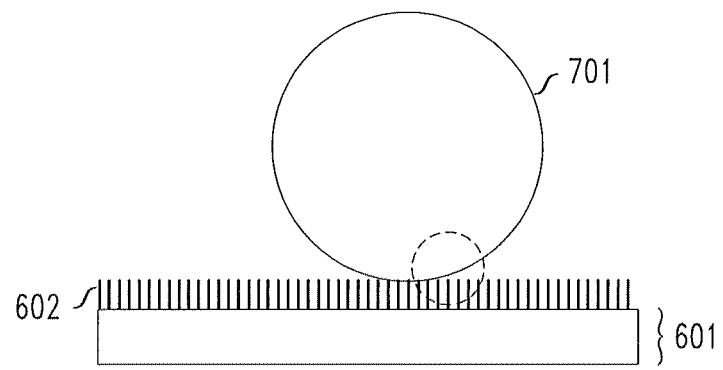
FIG. 8A shows a cross section of the droplet and nanostructure feature pattern of FIG. 7A.
Figure 8B:
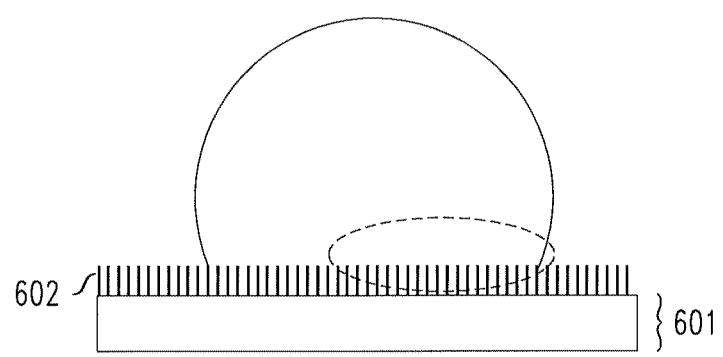
FIG. 8B shows a cross section of the droplet and nanostructure feature pattern of FIG. 7C.

FIGS. 8A and 8B show a cross-section illustration of the interactions between the nanostructured surface 601 of FIG. 6 and droplets of different liquids. FIG. 8A represents, for example, the droplet of water 701 of FIG. 7A. Due to the relatively high surface tension of the water, along with the intra-pattern characteristics of the nanostructures, droplet 701 is suspended on the tops of the nanoposts 602 (shown in greater detail in FIG. 6) and, as previously discussed, has a very high angle of contact with the nanostructured surface 601. As a result, droplet 701 experiences very low flow resistance. FIG. 8B represents, illustratively, the droplet 703 of cyclopentanol of FIG. 7C. Compared to the droplet 701 of water of FIG. 8A, the droplet 703 of cyclopentanol is not suspended on the tops of the nanoposts 602. Instead, because of the relatively low surface tension of the liquid, the droplet 703 completely penetrates the surface 601, thereby coming into contact with the solid surface underlying the nanoposts 602. The droplet has a low angle of contact, relative to the droplet 701 of FIG. 8A and, due to the complete penetration of the nanostructured surface 601, experiences a relatively high flow resistance.

Figure 1:
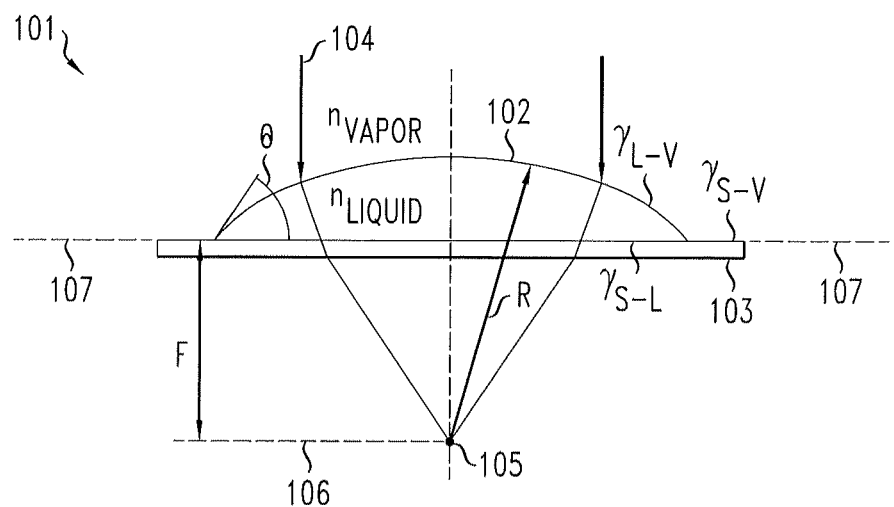
FIG. 1 shows a prior art microlens device that illustrates the interaction of a liquid disposed on a substrate.
Figure 2:
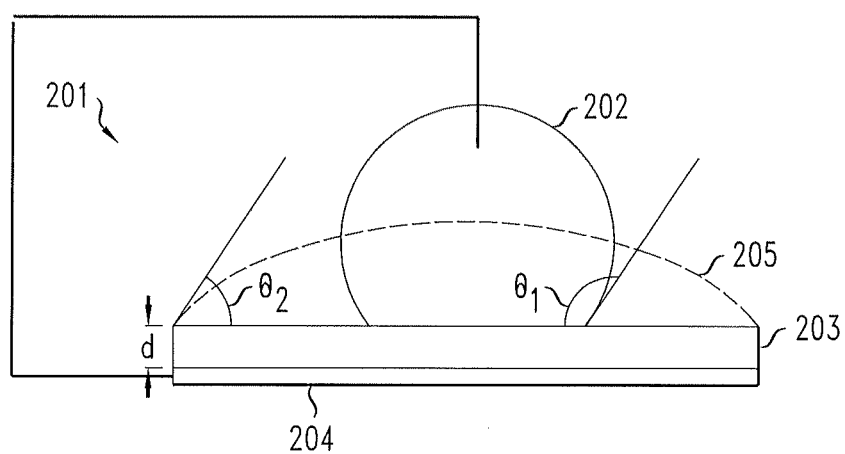
FIG. 2 shows how prior art electrowetting principles used with the microlens of FIG. 1 can be used to move the droplet in a predetermined direction across a substrate.
Figure 3A:
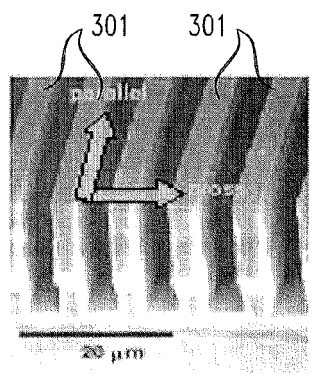
FIG. 3A shows a prior art microline surface.
Figure 3B:
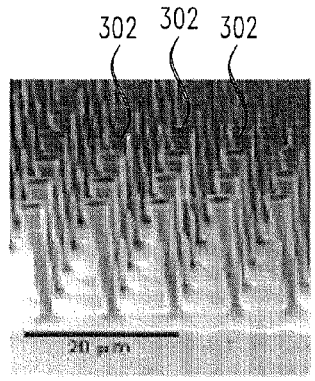
FIG. 3B shows a prior art micropost surface.
Figure 3C:
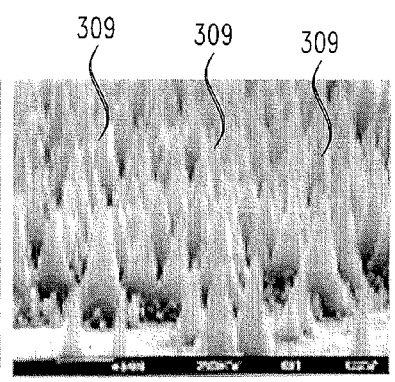
FIG. 3C shows a prior art nanopost surface.
Figure 3D:
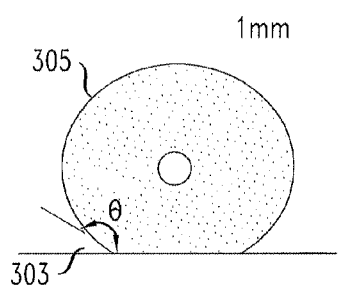
FIG. 3D shows a droplet of liquid disposed on the prior art surface of FIG. 3A and the corresponding contact angle that results between the droplet and that surface.
Figure 3E:
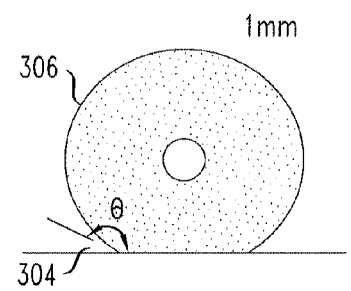
FIG. 3E shows a droplet of liquid disposed on the prior art surface of FIG. 3B and the corresponding contact angle that results between the droplet and that surface.
Figure 3F:
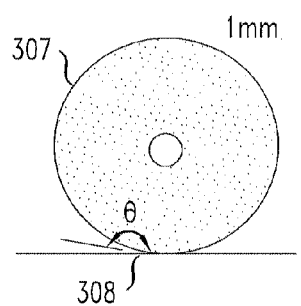
FIG. 3F shows a droplet of liquid disposed on the prior art surface of FIG. 3C and the corresponding contact angle that results between the droplet and that surface.
Figure 5:
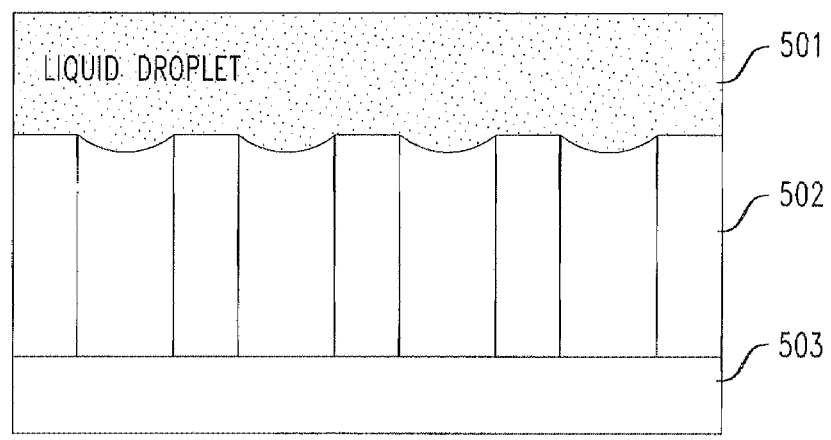
FIG. 5 shows an illustrative prior art device wherein a liquid droplet is disposed on a nanostructured feature pattern
Figure 9A:
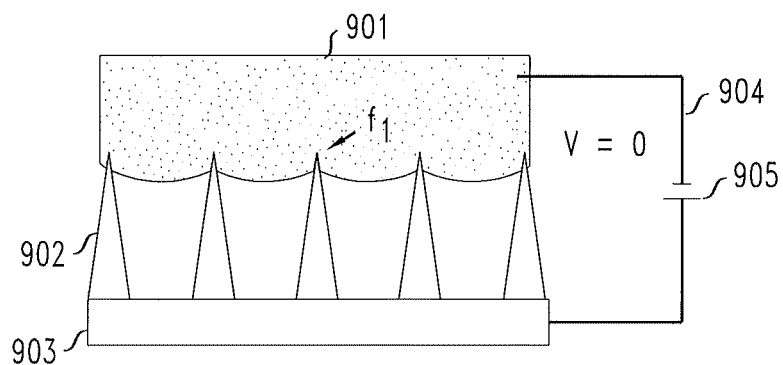
FIGS. 9A and 9B show a device in accordance with the principles of the present invention whereby the electrowetting principles of FIG. 2 are used to cause a liquid droplet to penetrate a nanostructure feature pattern.
Figure 9B:
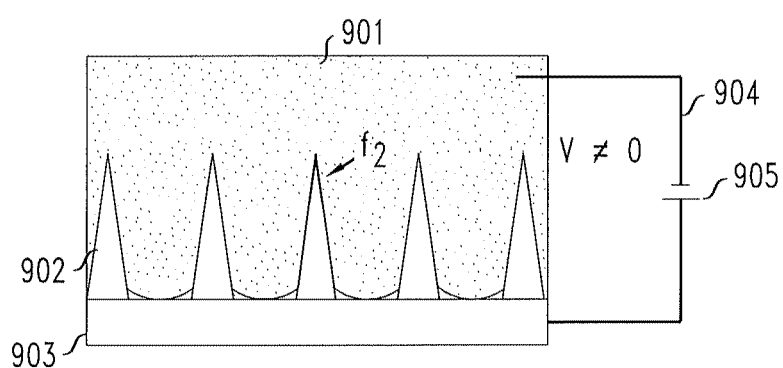

The present inventors have recognized that it is desirable to be able to control the penetration of a given liquid into a given nanostructured or microstructured surface and, thus, control the flow resistance exerted on that liquid as well as the wetting properties of the solid surface. FIGS. 9A and 9B show one embodiment in accordance with the principles of the present invention where electrowetting, similar to that used in the illustrative microlens of FIG. 2, is used to control the penetration of a liquid into a nanostructured surface.

Figure 10:
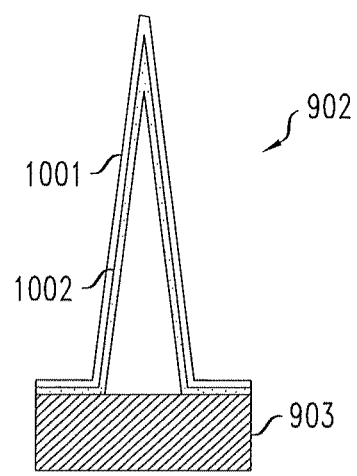
FIG. 10 shows the detail of an illustrative nanopost of the nanostructure feature pattern of FIGS. 9A and 9B.

Referring to FIG. 9A, a droplet 901 of conducting liquid is disposed on nanostructure feature pattern of conical nanoposts 902, as described above, such that the surface tension of the droplet 901 results in the droplet being suspended on the upper portion of the nanoposts 902. In this arrangement, the droplet only covers surface area $f_1$ of each nanopost. The nanoposts 902 are supported by the surface of a conducting substrate 903. Droplet 901 is illustratively electrically connected to substrate 903 via lead 904 having voltage source 905. An illustrative nanopost is shown in greater detail in FIG. 10. In that figure, nanopost 902 is electrically insulated from the liquid (901 in FIG. 9A) by material 1001, such as an insulating layer of dielectric material. The nanopost is further separated from the liquid by a low surface energy material 1002, such as a well-known fluoro-polymer. Such a low surface energy material allows one to obtain an appropriate initial contact angle between the liquid and the surface of the nanopost. It will be obvious to one skilled in the art that, instead of using two separate layers of different material, a single layer of material that possesses sufficiently low surface energy and sufficiently high insulating properties could be used.

FIG. 9B shows that, by applying a low voltage (e.g., 10-20 volts) to the conducting droplet of liquid 901, a voltage difference results between the liquid 901 and the nanoposts 902. The contact angle between the liquid and the surface of the nanopost decreases and, at a sufficiently low contact angle, the droplet 901 moves down in the y-direction along the surface of the nanoposts 902 and penetrates the nanostructure feature pattern until it complete surrounds each of the nanoposts 902 and comes into contact with the upper surface of substrate 903. In this configuration, the droplet covers surface area $f_2$ of each nanopost. Since $f_2 \gg f_1$, the overall contact area between the droplet 901 and the nanoposts 902 is relatively high and, accordingly, the flow resistance experienced by the droplet 901 is greater than in the embodiment of FIG. 9A. Thus, as shown in FIG. 9B, the droplet 901 effectively becomes stationary relative to the nanostructure feature pattern in the absence of another force sufficient to dislodge the droplet 901 from the feature pattern.

Figure 11:
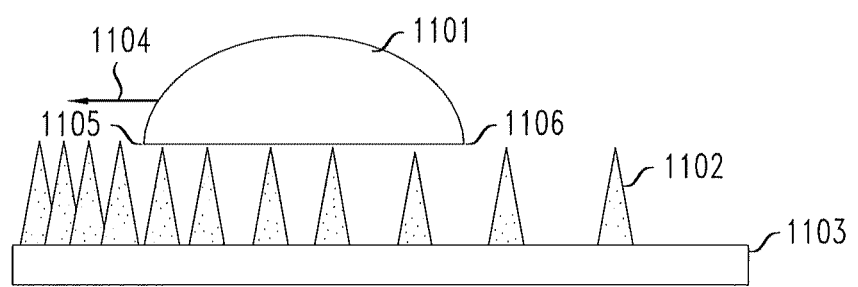
FIG. 11 shows how, by placing a droplet on a nanostructure feature pattern with having a varied density of nanoposts, the droplet will move toward the area of highest density of nanoposts.

FIG. 11 shows an illustrative device in accordance with the principles of the present invention whereby, instead of moving the droplet in the y-direction to penetrate the nanostructure feature pattern, the nanostructures (nanoposts 1102 in this illustrative embodiment) are arranged such that the droplet 1101 moves laterally in the x-direction 1104. Specifically, the nanoposts 1102 are arranged so that the density of nanoposts 1102 increases in the x-direction 1104. This increased density will lead to a lower contact angle at the leading edge 1105 of the droplet relative to the contact angle at the trailing edge 1106 of the droplet. The lower contact angle at edge 1105 leads to a lower force in the x-direction applied to the droplet 1101 than does the relatively higher contact angle at edge 1106. Thus, the droplet 1101 will "drift" in the x-direction 1104 toward the area of higher density of nanoposts 1102 as the liquid droplet 1101 attempts to achieve equilibrium. Thus, by placing the highest density of nanoposts at that location at which it is desired to have the liquid disposed on the surface, a liquid droplet can be initially disposed at another location on the surface and it will autonomously move toward that area of highest density.

Figure 12:
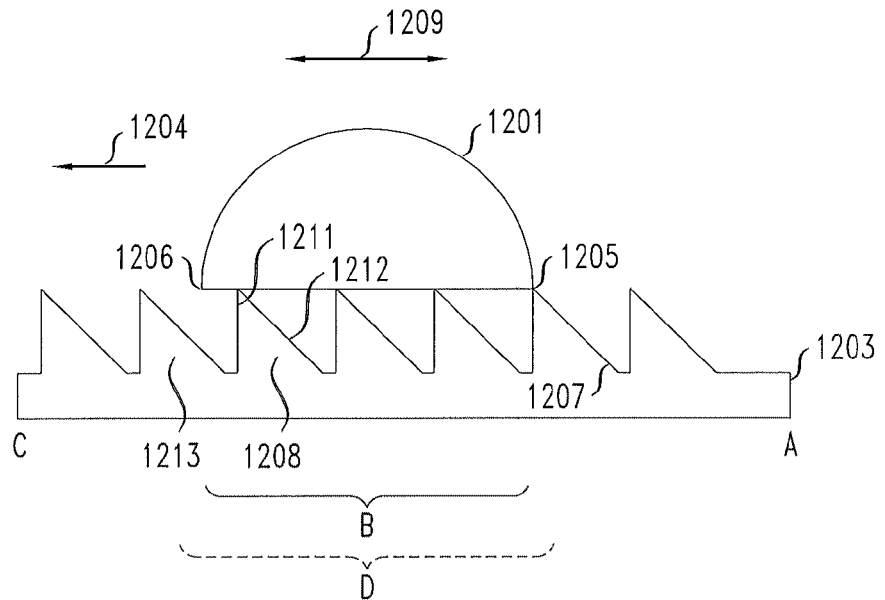
FIG. 12 shows how, by placing a droplet on a nanostructure feature pattern with nanoposts arranged in a saw-toothed pattern, the droplet will move in a known direction relative to that pattern.

While the movement achieved by the illustrative embodiment of FIG. 11 allows for a droplet to move to a final equilibrium location at the area of highest nanostructure density, it may also be desirable to reverse this movement away from the area of highest density. FIG. 12 shows one embodiment in accordance with the principles of the present invention that enables such a reversible movement. Specifically, FIG. 12 shows a droplet 1201 disposed on a surface having nanostructures 1202 arranged in sawtooth configuration. At equilibrium, the droplet will remain stationary in position B, just as it would with a nanopost feature pattern such as that exemplified by FIG. 8A. However, when a time-periodic excitation is applied to the droplet 1201, it will begin to drift in direction 1204. Such a periodic excitation may be generated, illustratively, by an alternating voltage applied to specific nanostructures 1202 or, alternatively, by ultrasound of an amplitude and frequency that disturbs the equilibrium of the droplet 1201. One skilled in the art will recognize that many different voltages, frequencies and amplitudes of sound waves may be used to generate the force necessary to disturb the equilibrium of the droplet 1201. Additionally, it will also be obvious to one skilled in the art that this excitation may be generated by many different methods.

The movement of droplet 1201 begins because, when disturbed, the droplet will periodically change the size of its contact spot and, thus, the edges 1205 and 1206 of the droplet 1201 will move back and forth over the nanostructures 1207 in the feature pattern. However, due to the asymmetric shape of the nanostructures 1207, the contact angle hysteresis at edge 1206 of the droplet relative to the surface will be lower than the contact angle hysteresis at edge 1205. In other words, in moving back and forth over the surface, it is much more difficult for the droplet 1201 to travel up the vertical face 1211 of, for example, feature 1208 than it is for the droplet 1201 to travel up face 1212 of feature 1208. Accordingly, once the droplet has crossed over a particular nanostructure in direction 1204, it will tend not to move back in the opposite direction and will establish a new equilibrium position, such as position D. If the time-periodic excitation (such as ultrasound) continues, the droplet will continue to travel back and forth across the surface until it crosses over the next nanostructure 1213 in direction 1204. Once again, the droplet will tend not to move back after crossing nanostructure 1213 and will attain yet another new equilibrium position in direction 1204. As a result, by continuing the periodic excitation, the droplet will stochastically move in direction 1204.

By combining the embodiment of FIG. 12 with areas of higher density of nanostructures, such as shown in the embodiment of FIG. 11, reversible lateral movement of the droplet 1201 may be achieved. For example, referring once again to FIG. 12, if an area of higher density of nanostructures 1202 is located at location A on the surface, the droplet 1201 will, as described above, tend to move toward location A absent any counteracting force. However, if the illustrative sawtooth pattern of FIG. 12 is used coupled with, illustratively, a disturbing force generated by ultrasound to disturb the equilibrium of the droplet 1201, the force tending to move the droplet toward location A (the higher density of nanostructures) will be overcome and the droplet 1201 will move in direction 1204 toward location C on the surface. If the force is removed (i.e., the ultrasound source is turned off), the droplet 1201 will once again tend to move toward the highest density of nanostructures at location C. Thus, reversible lateral motion is achieved.

Figure 13A:
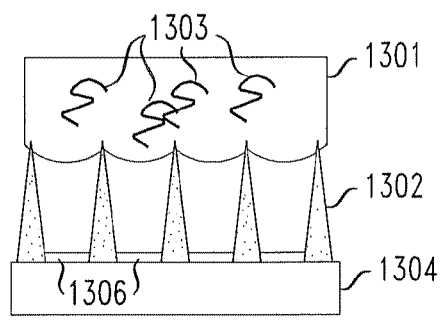
FIGS. 13A and 13B show a chemical or biological detector in accordance with the principles of the present invention.
Figure 13B:
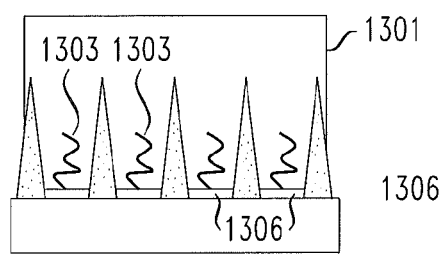

Cumulatively the illustrative embodiments of FIGS. 9A, 9B, 10, 11 and 12 show that it is possible, by using the principles of the present invention, to desirably move a droplet of liquid laterally along a surface with almost no flow resistance and to also move the droplet vertically such that the droplet penetrates that surface at a predetermined location and becomes practically immobile. Many applications can be found for such movement possibilities. For example, FIGS. 13A and 13B show an embodiment of a biological or chemical detector that uses the principles of the present invention. Referring to FIG. 13A, droplet 1301 is disposed on nanostructures 1302 similar to that shown in FIG. 9A. Detectors 1306, which are able to detect the desired biological or chemical compound 1303 are disposed on surface 1304. The liquid for droplet 1301 and the nanostructures 1302 are chosen such that, when the desired compound 1303 enters the liquid in a desired amount, the surface tension of the liquid drops and, as shown in FIG. 13B, the liquid 1301 penetrates the nanostructure pattern and comes into contact with the detectors 1306. When the compound 1303 comes into contact with the detectors 1306, an indication of such contact can be generate by well-known methods, such as via the generating of an electrical signal or the changing of the color of the detector.

It will be apparent to one skilled in the art that, in addition to being used as a detector, the embodiment of FIGS. 13A and 13B may also be used as a method of achieving a desired chemical reaction. For example, once again referring to FIG. 13A, it is possible to select a liquid for droplet 1301 such that the liquid already contains a chemical compound 1303. Detectors 1306 in this embodiment are fashioned out of a desired reactant compound that will achieve a desired reaction when in contact with element or compound 1303. These detectors/reactants 1306 are disposed between the nanostructures such that, when the liquid droplet penetrates the nanostructure feature pattern as shown in FIG. 13B, the two chemicals come into contact with each other and the desired reaction occurs. As previously described (e.g., in the discussion associated with FIGS. 9A and 9B, above), the droplet can be made to penetrate the feature pattern by either applying a voltage to the droplet or, alternatively, by using some method for lowering the surface tension of the liquid droplet 1301 (and, thus, the contact angle it forms with the surfaces of the nanostructures) such as, for example, increasing the temperature of the liquid droplet 1301.

Figure 14:
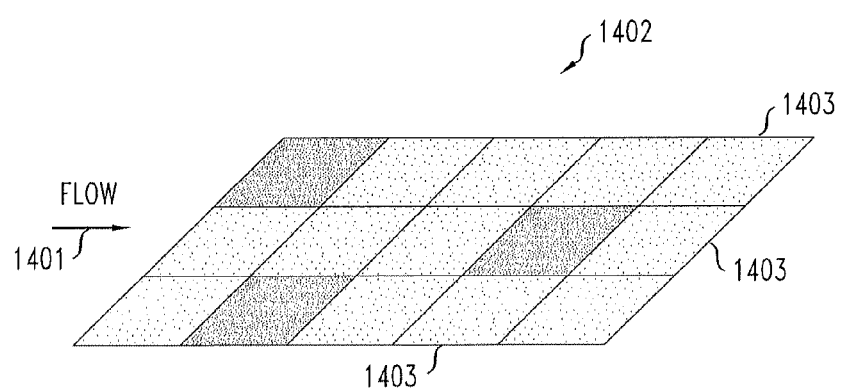
FIG. 14 shows how the detector of FIGS. 13A and 13B can be arranged in an array in able to detect multiple elements or compounds.

FIG. 14 shows a possible arrangement of the illustrative embodiments of FIGS. 13A and 13B, whether used as a chemical/biological detector or used in a chemical reaction application. Specifically, a liquid can be made to flow in direction 1401 across the surface of array 1402, which has a predetermined arrangement of nanostructures patterned on its surface. Each of areas 1403 may, for example, have detectors/reactants (such as 1306 in FIGS. 13A and 13B) disposed between the nanostructures that are suited, for example, for detecting or reacting with a different chemical/biological compound. Thus, if used as a detector, the array 1402 of FIG. 14 could be used to detect multiple different compounds. If used as a chemical reactor, each of the areas could be designed so as to react with only a certain compound to achieve the desired reactions.

Figure 15:
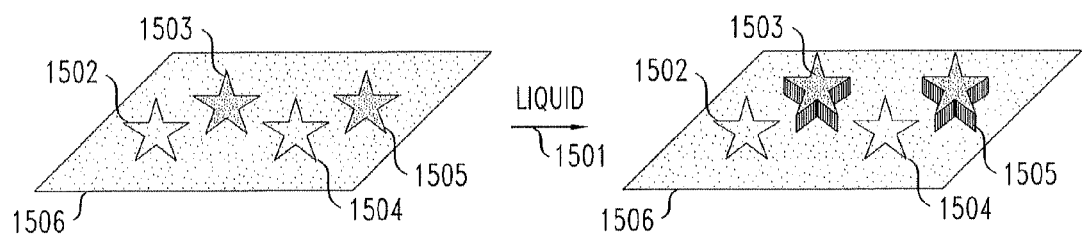
FIG. 15 shows how a pattern can be made in accordance with the principles of the present invention.

Another use for the principles of the present invention is illustratively shown in FIG. 15. Specifically, FIG. 15 shows how selective patterning of a desired pattern onto a surface can be achieved by utilizing the principles of the present invention. In this figure, a desired pattern (in this case star-shaped patterns 1502, 1503, 1504 and 1505) is defined on a substrate 1506 which is characterized by nanostructure features. It is a desirable goal in such a patterning application to cause the liquid to move within the patterns 1502-1505 and to the remain in those patterns. One method of accomplishing this goal is to use the well-known voltage differential electrowetting, described above, between a liquid flowing in direction 1501 across the substrate and the nanostructures within star-shaped patterns 1503 and 1505. When the liquid passes across the surface, the liquid only penetrates between the nanostructures within those two patterns, thus becoming practically immobile. Due to this resulting immobility, when the liquid flow is removed, liquid remains only within patterns 1503 and 1505.

An alternative method of causing a liquid to move to the star-shaped patterns in a patterning application is to use a varying density pattern, such as that illustrated in FIG. 11, to move the liquid to a relatively dense pattern, such as pattern 1502, and then held in place by such electrowetting. Electrowetting could also be used in a patterning (as well as other applications) to more fully wet the star-shaped patterns of FIG. 15. Specifically, it may be difficult, using the aforementioned varying density pattern to move the droplet to a complex pattern, such as star-shaped pattern 1502, to cause the liquid to move entirely to the tips 1507 of the pattern. However, by applying sufficient electrowetting voltage, total wetting may be obtained.

Thus, it is possible to pattern a liquid within specific and complex areas on a substrate such as substrate 1506. By selecting a well-known liquid susceptible to polymerization (such as, for example, an acrylic-based monomeric liquid including, but not limited to, the NA72 optical adhesive manufactured by Norland, Inc.), and applying, for example, ultraviolet light to that liquid, a polymerized, hardened material can be achieved that conforms to patterns 1503 and 1505. It will be obvious to one skilled in the art that this polymerization process can be used with any of the illustrative embodiments herein in order to move a liquid to a desired location, cause the-liquid to penetrate the nanostructured feature pattern, and then fix the droplet in a polymerized state in that location.

Figure 16A:
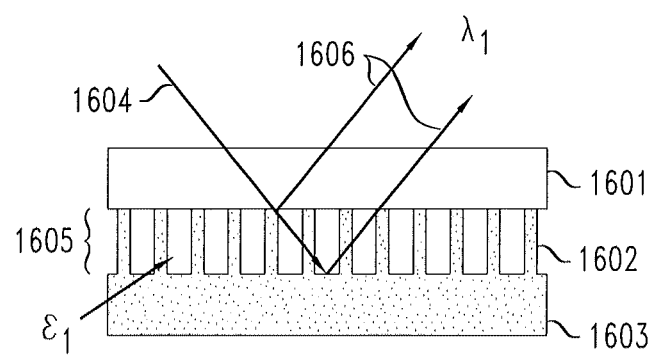
FIGS. 16A and 16B show a diffractive grating in accordance with the principles of the present invention.
Figure 16B:
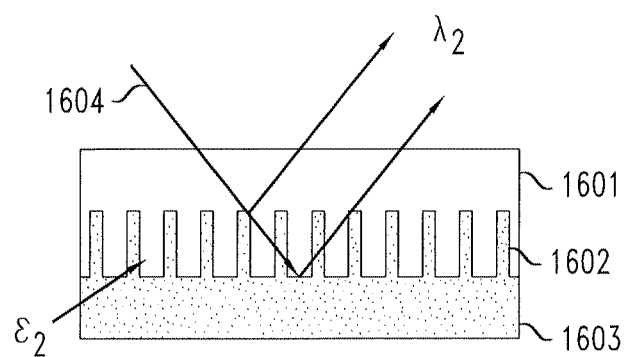

FIGS. 16A and 16B show another useful application of the principles of the present invention. Specifically, in FIG. 16A, an optical diffractive grating is shown wherein a droplet 1601 of liquid which is transparent to at least some wavelengths of light is disposed on nanostructures 1602. Nanostructures 1602 are, in turn, disposed on surface 1603 which is, for example, a silicon substrate, as previously described. When light beam 1604 is incident upon droplet 1601, at least some wavelengths pass through droplet 1601 and are reflected off of surface 1603 in such a way that the light travels along path 1606 back through the droplet of liquid. By passing through the liquid droplet 1601, then through area 1605 (having dielectric constant $\in_1$), and reflecting off of the underlying substrate 1603, various frequencies of light are filtered out (due to the difference in refractive index between the liquid and area 1605) and only wavelength $\lambda_1$ emerges to propagate in the predetermined direction. FIG. 16B demonstrates that, by causing the liquid droplet 1601 to penetrate the nanostructures 1602 (through the use of one of the methods described above), the dielectric constant of area 1605 changes to $\in_2$, thus changing the refractive index of the medium through which the light travels and, therefore, only $\lambda_2$ will emerge to propagate in the predetermined direction. Thus, one skilled in the art will recognize that a tunable diffractive grating is created that, when the liquid 1601 penetrates the nanostructure feature pattern, allows a different wavelength of light to pass through the grating, compared to when the liquid 1601 is not penetrated into the feature pattern.

Figure 17A:
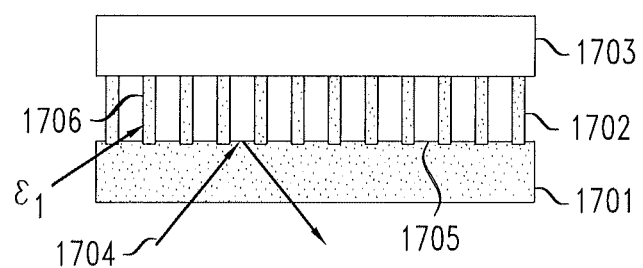
FIGS. 17A and 17B show a total internal reflection (TIR) mirror in accordance with the principles of the present invention.
Figure 17B:
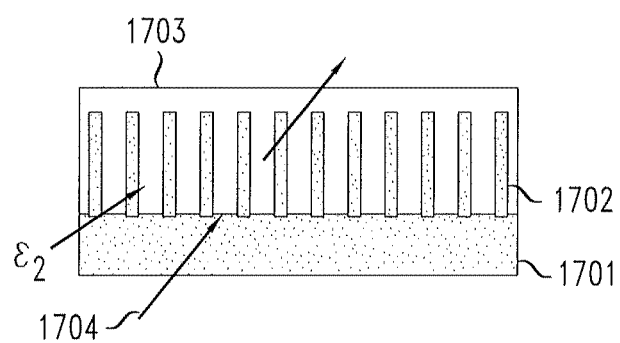

FIGS. 17A and 17B show another illustrative optical use of the principles of the present invention, specifically as a total internal reflection (TIR) mirror. Illustratively, referring to FIG. 17A, substrate 1701 (for example a glass substrate), which is transparent to at least one wavelength of light, supports a feature pattern of nanostructures 1702. Droplet 1703 is suspended on the nanostructures 1702 as described herein above. The substrate 1701 is positioned such that, when light beam traveling in direction 1704 passes through the substrate at a particular angle of incidence (that is a well-known angle depending on the wavelength of light) the light beam is reflected when it encounters the boundary of the upper surface 1705 and the gas 1706. This reflection is achieved because the gas (e.g., air) has a dielectric constant $\in_1$ that results in the refractive index of the gas 1706 to be lower than that of the substrate 1701.

FIG. 17B shows a droplet 1703 that has penetrated the nanostructure feature pattern 1702 (once again, via the methods described above). The penetrated area of the nanostructure feature pattern has a dielectric constant $\in_2$ that results in a refractive index higher than that of the substrate 1701. As a result, the light passes through the droplet 1703 and is not reflected. One skilled in the art will recognize the specific angles of incidence of a light beam of specific wavelengths that, when combined with an appropriate substrate material, gas and droplet liquid, will achieve the tunable reflective properties described herein and shown in FIGS. 17A and 17B.

Figure 18A:
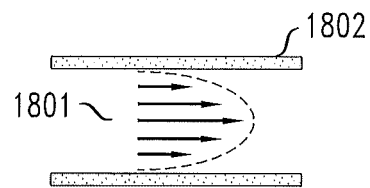
FIGS. 18A, 18B and 18C show a microfluidic mixer in accordance with the principles of the present invention.
Figure 18B:
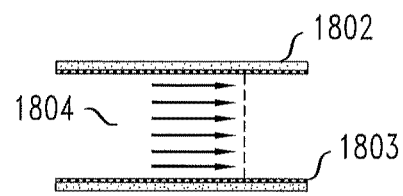
Figure 18C:
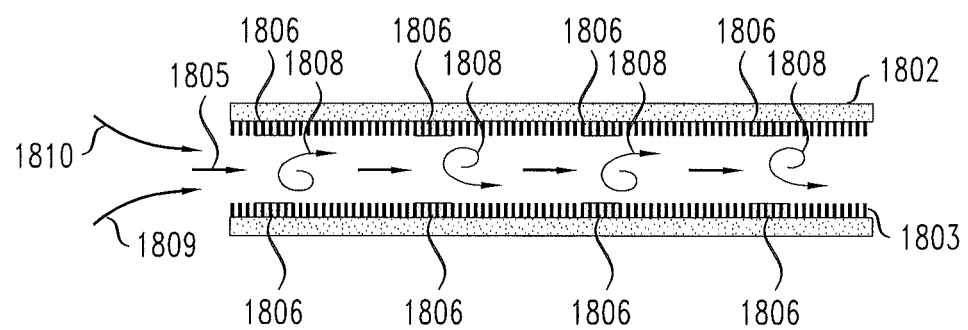

FIGS. 18A, 18B and 18C show another embodiment in accordance with the principles of the present invention whereby a nanostructure feature pattern is disposed on the interior wall of a channel, such as a microfluidic tube 1802. FIG. 18A shows that, if no nanostructures are used on the interior surface of the tube, as in prior microfluidic tubes, the flow resistance caused by the friction between the interior wall and the liquid leads to a reduced velocity of the liquid close to the interior wall as it travels through the channel. The velocity of the liquid at different distances from the interior wall of the channel is represented by the velocity vector profile 1801. This vector profile 1801 shows that liquid in the center of the channel travels fastest (longer velocity vector), and liquid immediately adjacent to the wall travels slowest (shorter velocity vector). As a result of this flow resistance at the inner wall larger pumps that consume relatively high amounts of power are required to pump the liquid through the microfluidic channel 1802. FIG. 18B shows how, by disposing a nanostructure feature pattern 1803 on the internal wall of the microfluidic channel 1802, the flow resistance exerted on the liquid is advantageously reduced. This is represented by the velocity vector profile 1804 of the liquid, which shows how the velocity of the liquid adjacent to the walls of the channel 1802 is approximately equal to the velocity of the liquid in the center of the channel. Due to the lowering of the flow resistance resulting from the use of nanostructure feature pattern 1803, the pumps required to pump the liquid through the channel are smaller and advantageously require relatively low power to operate.

In microfluidic applications it is often desirable to mix different liquids traveling through two or more channels. For example, it is useful to mix DNA and a reagent traveling in separate channels for use in integrated microfluidic biochemical analysis systems. In such systems, this mixing precedes the electrophoresis process through which genetic information is derived from the DNA sample. Prior efforts to mix multiple channels have, disadvantageously, taken a relatively long distance to fully accomplish this mixing. FIG. 18C shows a mixer in accordance with the principles of the present invention. This mixer is useful if, for example, it is desired to combine the flows of two different liquids flowing, illustratively, in directions 1809 and 1810. As discussed above, by disposing a nanostructure feature pattern 1803 on the internal walls of the channel, a relatively low flow resistance is achieved through the channel. As discussed above, the flow resistance at certain areas, such as areas 1806, along the wall can be increased by selectively causing the liquid to penetrate the nanostructure feature pattern by, for example, increasing the temperature of discrete areas 1806 of the nanostructured feature pattern or, alternatively, creating a voltage differential between the liquid and areas 1806 of the feature pattern. Thus, the flow 1805 through the mixer of FIG. 18C is characterized by areas of low flow resistance, with areas of high flow resistance to the liquid adjacent to areas 1806 of the microfluidic channel 1802. Therefore, strongly disturbed flow, such as that represented by flows 1808, are created. This disturbed flow greatly enhances the mixing process and accomplishes mixing of two or more liquids over a relatively short distance. Additionally, since the mixer of FIG. 18 enables dynamic control of the interface properties between the liquid and the surface, such as flow resistance, the mixer of FIG. 18 can be actively tuned.

Figure 19:
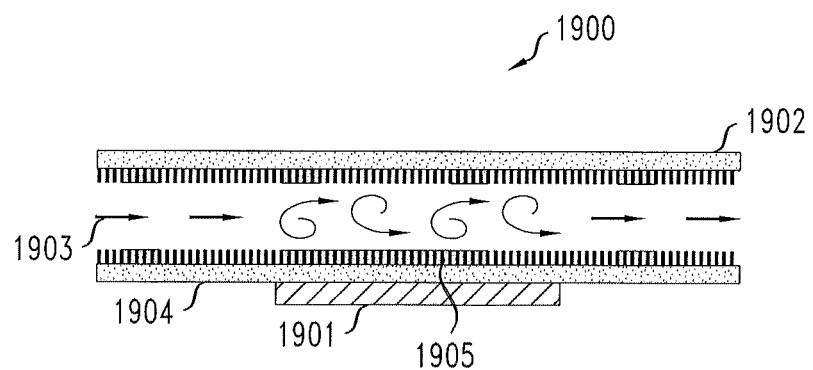
FIG. 19 shows a heat dissipation device in accordance with the principles of the present invention.

FIG. 19 shows another embodiment of the present invention whereby a nanostructured feature pattern is disposed on the internal walls of a channel, such as that advantageously used in a heat dissipation device. Heat dissipation is a primary concern in many applications, such as dissipating the heat generated by electronic devices. The performance and overall life of an electronic device is often adversely affected by excess heat. Device 1901 is an exemplary heat-generating device, such as a central processing unit or other processor in a computer. Channel 1902 is placed adjacent to or, preferably, in contact with device 1901. When no heat is generated by device 1901, the liquid in channel 1902 experiences low flow resistance, as shown in FIG. 18B. Illustratively, the liquid is chosen such that, when a predetermined amount of heat is experienced, the surface tension of the liquid drops and the liquid wets the surface of wall 1904. One skilled in the art will recognize that other methods of wetting the nanostructured surface may also be utilized, such as the aforementioned electrowetting method illustrated in FIGS. 9A and 9B.

When device 1901 generates a sufficient amount of heat, the heat is transferred through the channel wall 1904. The surface tension of the liquid traveling within the channel in direction 1903 drops and, as a result, the liquid penetrates the nanostructure feature pattern on the interior walls of the channel in area 1905 of the nanostructure feature pattern. As such, the liquid in area 1905 comes in direct contact with wall 1904 and more efficiently transfers heat from the wall to the liquid flowing in direction 1903. As will be recognized by one skilled in the art, the disturbed flow 1906 that results from the penetration of the liquid in area 1905 is more conducive to heat dissipation than is an undisturbed laminar flow. While prior liquid-based heat dissipation attempts (not relying on a nanostructured feature pattern) were adequate for dissipating heat to a certain extent, the embodiment of FIG. 19 is advantageously capable of dissipating significantly more heat.

The foregoing merely illustrates the principles of the invention. It will thus be appreciated that those skilled in the art will be able to devise various arrangements which, although not explicitly described or shown herein, embody the principles of the invention and are within its spirit and scope. For example, one skilled in the art, in light of the descriptions of the various embodiments herein, will recognize that the principles of the present invention may be utilized in widely disparate fields and applications. For example, moving a droplet of liquid and causing it to remain in a desired stationary location is useful in the self-assembly of various devices, such as microlenses. By using the principles disclosed herein, a microlens can be placed on a surface and will autonomously move to a desired location at which point it remains stationary. In another potential embodiment of the present invention, the nanostructured or microstructured surfaces of the present invention are used in a display device. By controlling the movement of one or more liquids inside the display through the use of the principles disclosed herein, different images can be displayed.

All examples and conditional language recited herein are intended expressly to be only for pedagogical purposes to aid the reader in understanding the principles of the invention and are to be construed as being without limitation to such specifically recited examples and conditions. Moreover, all statements herein reciting aspects and embodiments of the invention, as well as specific examples thereof, are intended to encompass functional equivalents thereof.

What is claimed is:

1. An apparatus, comprising:
a substrate having a surface with a plurality of nanostructures or microstructures thereon, said plurality of nanostructures or microstructures being able to support a droplet of liquid disposed on tops thereof wherein:
at least a portion of said nanostructures or microstructures has an increased spatial density along a predetermined direction on said surface, such that a leading edge of said droplet that is closer to said increased spatial density has a lower contact angle than a trailing edge of said droplet that is farther away from said increased spatial density, and
said predetermined direction leads to a location on said substrate having a highest spatial density of said nanostructures or microstructures.

2. The apparatus of claim 1, wherein there is a monotonically decreasing distance between adjacent ones of said portion of said nanostructures or microsructures along said predetermined direction.

3. An apparatus, comprising:
a substrate having a surface with a plurality of nanostructures or microstructures thereon, said plurality of nanostructures or microstructures being able to support a droplet of liquid disposed on tops thereof wherein:
for at least a portion of said nanostructures or microstructures, each of said nanostructures or microstructures are configured as same asymmetrical saw-tooth shaped posts having a same orientation of said asymmetrical saw-tooth shape along a predetermined direction on said surface, such that a leading edge of said droplet that is closer to a vertical face of said saw-tooth shaped posts has a lower contact angle than a trailing edge of said droplet that is closer to a sloped face of said saw-tooth shaped posts, and
said predetermined direction leads to a location on said substrate having a different portion of said nanostructures or microstructures with a highest spatial density of said nanostructures or microstructures.

4. The apparatus of claim 3, wherein for said portion there is a constant distance between said vertical faces of adjacent ones of said nanostructures or microstructures.

5. An apparatus comprising:
a surface having a pattern of features, said surface including:
a pattern of nanoposts or microposts capable of supporting a droplet of liquid over said surface and having an intra-pattern characteristic adapted to produce a controlled motion of said droplet in a predetermined direction along the surface, wherein:
at least a portion of said pattern of nanoposts or microposts is configured to cause a contact angle of a leading edge of said droplet to be lower than a contact angle of a trailing edge of said droplet in said predetermined direction,
either a spatial density of said nanoposts or microposts increases along said predetermined direction, or, said nanoposts or microposts have asymmetric shapes and form a sawtooth pattern along said predetermined direction, and
said predetermined direction leads to a location on said substrate having a different portion of said nanostructures or microstructures with a highest spatial density of said nanostructures or microstructures.

6. The apparatus of claim 5, wherein said spatial density of said of nanoposts or microposts increases along said predetermined direction.

7. The apparatus of claim 6, wherein adjacent ones of said nanoposts or microposts are separated by a monotonically increasing distance along said predetermined direction.

8. The apparatus of claim 5, wherein said nanoposts or microposts have said asymmetric shapes and form said sawtooth pattern along said predetermined direction.

9. The apparatus of claim 8, wherein vertical faces of adjacent ones of said portion of nanoposts or microposts are separated by a constant distance.

10. The apparatus of claim 5, wherein said spatial density of said nanoposts or microposts is higher in one area of said surface.

* * * * *